United States Patent [19]

Vaseen

[11] 4,302,905
[45] Dec. 1, 1981

[54] GROWING CELLS OF PLANTS IN A MULTI-MEDIA HYDROPONIC ENVIRONMENT

[76] Inventor: Vesper A. Vaseen, 9840 W. 35th Ave., Wheat Ridge, Colo. 80033

[21] Appl. No.: 146,227

[22] Filed: May 5, 1980

[51] Int. Cl.³ ............................................. A01G 31/02
[52] U.S. Cl. .......................................... 47/58; 47/59
[58] Field of Search ............................... 47/58, 59–65

[56] References Cited

U.S. PATENT DOCUMENTS

| | | | |
|---|---|---|---|
| 3,514,900 | 6/1970 | McDade | 47/58 |
| 3,683,550 | 8/1972 | Corlett et al. | 47/58 |
| 3,710,805 | 1/1973 | Tamaki et al. | 47/58 X |
| 3,816,960 | 6/1974 | Gudin et al. | 47/58 |

Primary Examiner—Robert E. Bagwill

[57] ABSTRACT

Living cells of plants, such as Thallophyta and Embryophyta are grown at an accelerated rate in a multi-medium hydroponics mixture consisting of a carbon dioxide gas impregnated inert, nonionic, non-aggressive, liquid medium which is non-miscible with water; and an aqueous hydroponic nutrient liquid medium; as compared to the single medium nutrient aqueous liquid medium.

The process consists of growing clone cells, or callus, in a mechanically mixed suspension of a nutrient hydroponic liquid, made up of water and selected soluble mineral nutrients; and supplementing the growing cells need of carbon, the principal cell mass, with carbon dioxide carried dissolved as a non-ionic gas in an inert, non-hypertonic, non-hypotonic liquid; rather than use of "sugar".

Mixing the nutrient aqueous hydroponic liquid and the inert carrier liquid provides not only the exchange of carbon dioxide to the cells, but receives from the cell and the aqueous liquid the cell evolved oxygen; thus expediting further the healthy growth of live plant cells.

Live plant clone cells are separated from the liquids, as product, and the liquids replenished for recycle use.

1 Claim, No Drawings

4,302,905

GROWING CELLS OF PLANTS IN A MULTI-MEDIA HYDROPONIC ENVIRONMENT

INTRODUCTION

The growth of clone cells of specific parts of living plants known to the art and science of Botany as "Callus" cells and as the cells mature as diversified cells; has been a laboratory experimental art and science, and of minimal commercial value for many years.

References to the techniques of growing callus and plant diversified cells are many among which are: (1) plant tissue and cell culture, botanical monographs, Vol. 11; edited by H. E. Street, Botanical Laboratories, University of Leicester England; University of California Press, 1973; (2) a broad spectrum tissue culture experiment with tobacco (nicotiana tabacum) tissue cells; R. A. deFossard, Aung Myint and Edward C. M. Lee; Department of Botany, the University of New England, Armidale, N.S.W. 2351 Australia; Physiol. Plant, 31:125-130, 1974; (3) Single cell clones, H. E. Street; Plant tissue and Cell Structure, Botanical Monographs, Vol. 11, 1973.

Growth of clone and diversified plant cells has prior to this invention been limited to a few ounces of grams of cells, developed principally for the purposes of plant growth study, development of mutations, and/or potential for plant disease control; along with growth of nursery clone plants from clone cells.

PRIOR ART HISTORY

In or just prior to 1970, a commercially feasible method of rapidly reproducing orchid plants was developed by Everest McDade, and patented June 2, 1970, U.S. Pat. No. 3,514,900. This consists of dividing growing undifferentiated plant tissue from a specific orchid plant, and a plurality of tissue masses to differentiate and mature into a plurality of identical plants. The plant cells grown in a nutrient aqueous hydroponic solution.

A similar patent was issued Aug. 15, 1972 to Donald A. Corlett, Jr. and Panos D. Caldis for reproducing large numbers of pineapple plants using a three-stage plant tissue culture technique; these also grown in a nutrient aqueous hydroponic solution.

Einosuke Tamaki, Masao Kobari, Fumihiro Miyanowaki, Kunio Kato, Ko Nishida and Yukio Shimizu received Jan. 16, 1973, U.S. Pat. No. 3,710,805, for a process to grow tobacco cells in a suspension liquid, then filter them out, using the matte of tobacco on the filter paper as a means of producing cigarettes.

A further improvement in growth of callus cells by Gudin, et al, was given June 18, 1974, U.S. Pat. No. 3,816,960. This involves a refined photosynthetic ability to enhance cell growth.

Until this discovery and disclosure, no hydroponic process has used a multi-media one of which is an inert, non-ionic carbon dioxide carrier liquid, for providing the cells carbon requirements, from carbon dioxide rather than from "sugar".

SUMMARY OF THE INVENTION

Although the term "plant cells" has been used herein, the close relationship of plant and animal as cells, makes the process equally adaptable to some types of animal cell growth by adjusting the environment to conform to animal rather than plant life.

The process starts with the development of a laboratory grown culture of selected live cells, wherein the ultimate object of the process is to grow commercial quantities of clone or diversified cells, specific selected cells are developed which provide the maximum quality and quantity of the desired type and kind of product. For example, if the product desired is principally carbohydrate, then clone or diversified plant cells are laboratory cultured to retain a high percentage of carbohydrate. The same selection process is used for proteins, or lipids.

The historical methods and rates of cell growth of specific clones of specific plant species is easily and accurately available either from the literature or by laboratory determination, for those versed in the arts and sciences of Botany.

The time required for the completion of mitosis (cell division), and cytokinesis (maturing for next mitosis), varies with different types of cells and in different species of plants. Growth rates are influenced by varying environmental conditions. In most dividing plant cells at temperatures of 21° C. (70° F.) to 27° C. (80° F.), the process of mitosis and cytokinesis are usually completed within 60 to 90 minutes. (The temperature range of mitosis is generally from 40° F. to 120° F.)

A selected quantity of culture cells of the species of plant selected and of the specific material desired, as grown under laboratory aseptic conditions, is provided to a mitosis or growth vessel which has previously been filled with the mixture of aqueous mineral nutrient supplying medium, and carbon dioxide dissolved in the inert carrier liquid; both of which have been adjusted to the preferred process temperature of between 16° C. (60° F.) and 43° C. (110° F.), previously laboratory determined as most efficient for the specific cells grown.

The cells are kept from clumping by mixing the total contents of the reaction vessel.

When the contents of the reaction vessel in the active zone reaches a predetermined solids to liquid relationship found to be most efficient for the specific cells grown and their total environment, a percentage of the vessel content liquid containing cells is removed and an equal amount of fresh liquids replaced in the vessel. The cells are separated from the liquids, and made available to whatever other processing as required for the specific use of the product cells. The spent hydroponic aqueous medium recovered from the separation of the cells is brought up to full nutrient strength for recycle use or disposed of as necessary. The inert carrier liquid of the non-ionic carbon dioxide to the growing cells, as removed with product cells, will contain dissolved oxygen produced by the cells. The inert liquid is stripped of the oxygen, which may be collected for salvage, then sterilized, if necessary, resaturated with carbon dioxide gas and returned to process recycle use.

The growth of cells species which require light energy to provide for photosynthesis, are provided light energy within the reaction vessel. Light energy requirements vary with plant species, and other environmental factors, and is provided at the vessel liquid surface at an intensity preferably of between 200 to 1000 foot candles.

The mitosis of cells produces a few mutations for each 1,000,000 cells. For this reason it is recommended process operations be concluded periodically and restarted with a new laboratory controlled culture.

PREFERRED EMBODIMENTS

The art and science of growing clones or diversifying plant cells in a multi-media hydroponics environment is taught hereafter by way of example. Those versed in the art and science of Botany and Aquacultures will not have difficulty adapting the process and methods of many species of plant cells as well as to specific plants, such as predominantly carbohydrate, protein or lipid.

For example, Samson Tobacco clones have been grown for many years in laboratories for the express purpose of developing mutant strains which have selective qualities, such as disease resistance.

Cultured cells, such as with this example, which are laboratory grown on Linsmaier and Skoog's basic medium; to which is added 6 ppm 2,4D; 0.5 ppm Kinetin; 0.1% yeast extract; and 0.1% malt broth extract; are acceptable callus cell growth techniques, which those versed in the arts and sciences of Botany and Callus Cells Growth will have no difficulty in growing same.

The non-ionic carbon dioxide is provided absorbed in an inert dielectric liquid. Two of the acceptable type liquids are the polyorganosiloxanes and the fluorocarbons.

For example, the polyorganosiloxane $(CH_3)_3 SiO (CH_3)_2 SiO_x Si(CH_3)_3$ is saturated with carbon dioxide gas, by mixing the gas with the liquid under aseptic conditions. Those familiar with methods of absorbing gases into a liquid will have no difficulty bubbling carbon dioxide gas through the inert carrier liquid and achieving a satisfactory saturation. Various inert liquids acceptable as the carbon dioxide gas carrier, due to their molecular structures, are highly soluble of gases. At atmospheric conditions, these liquids absorb greater than 20 volumes of carbon dioxide per volume of liquid.

For each gram of cells grown, approximately 0.71 grams of carbon dioxide is provided. The affinity, for example, of the polyorganosiloxane is approximately 0.275% by weight. If all the carbon dioxide is provided to the mixture at one time, 25.82 grams of polyorganosiloxane is required. Preferably the polyorganosiloxane is supplied with absorbed carbon dioxide for each mitosis doubling of cell growth, for example, 90 minutes at 21° C. and 60 minutes at 27° C.; carrying absorbed the quantity of carbon dioxide required for next selected growth period. For example, with 0.10 grams of cells in the mitosis vessel and growth rate at 27° C. of 0.10 grams new cells; then 0.071 grams of carbon dioxide is provided in 2.582 grams of polyorganosiloxane for the next hours growth.

The aqueous medium is preferably a conventional hydroponics soluble minerals nutrient in water. These combinations of mineral nutrients are commercially available from many sources, although for those versed in the art and science of hydroponics, the individual chemicals are used to manufacture a designed hydroponics liquid containing the necessary chemical and mineral nutrients.

Preferably the chemical constituent are mixed in the proportions of not less than:

| CHEMICAL | QUANTITY Oz. | Grams | SUPPLIED |
|---|---|---|---|
| Ammonium Sulphate | 1.5 | 43 | Nitrogen & Sulphur |
| Potassium Nitrate | 9 | 255 | Nitrogen & Potassium |
| Monocalcium Phosphate | 4 | 113 | Phosphorous & Calcium |
| Magnesium Sulphate | 6 | 170 | Magnesium & Sulphur |
| Calcium Sulphate | 7 | 198 | Calcium & Sulphur |
| Iron Sulphate | 0.04 | 1 | |
| Iron Sulphate | 0.04 | 1 | Iron |
| | 27.54 | 780 | |

The chemicals are mixed with sterile water preferably to have a total dissolved solids content of less than 350 mg/l, and free of plant toxic elements. The combined chemicals are mixed with the water preferably not to exceed 10 grams or ⅓ oz. per gallon.

The example used herein uses 300 ml side arm erlenmeyer flasks, each of which contains 50 ml of the aqueous nutrient solution above described. To this is added 33 ml of laboratory conditioned growth tobacco callus suspension containing approximately 2.5 million cells. It makes no difference as to the ratio of aqueous nutrient media to carrier liquid media, as long as the carrier liquid is made available to the mixture at a rate or quantity which always contains available carbon dioxide absorbed therein.

Preferably the inert carrier liquid is provided the mixture by having been saturated by carbon dioxide gas delivered through a 0.2 um millipore filter, with the carbon dioxide saturated carrier liquid then introduced to the aqueous nutrient solution and tobacco callus suspension by a Pasteur pipette.

Preferably all elements of the system be autoclaved prior to cell growth cycles.

Mixing is required to sufficiently provide a continually renewed interface between the non-miscible aqueous and inert carrier liquid. For this example an Eberback gyrotory shaker is used providing (80) eighty oscillations per minute. Those versed in the art and science of botanical cell growth will have no problem determining when mixing is adequate or too active and mechanical damage is done to the cells.

The continually renewed interface between the aqueous nutrient media and the inert carrier liquid is required to permit mass transfer of absorbed non-ionic carbon dioxide gas in the inert carrier liquid, to the aqueous at replacement rate the ionic carbon dioxide is removed from the aqueous by growing cell use of the carbon dioxide as its source of carbon.

Photosynthesis light energy, as required for conversion of the (aqueous) water by the cell metabolism to hydrogen and oxygen is preferably provided by artificial means on a continuous basis at an intensity of between 100 to 1,000 foot candles at the surface of the liquid suspension.

Optimum growth rate, that is, cell mitosis, is preferably at 27° C., although mitosis proceeds from 20° to 30° C.

Callus cells grown in the environment of both an aqueous nutrient, and a non-ionic carbon dioxide carrier liquid are produced at twice the rate as parallel grown callus cells, grown in only the aqueous nutrient hydroponic environment. Growth rate of callus suspensions is measured by measuring the depth of cells accumulation in the side arm of the flask.

I claim:

1. I claim a method of growing clones and diversifying cells of plants by use of a multi-media hydroponics consisting of an aqueous nutrient solution in conjunction with an inert, non-ionic liquid saturated with non-ionic carbon dioxide gas; consisting of:

growing laboratory cultures of acclimated callus or diversifying plant cells, by the method of, dissolving predetermined quantities of mineral nutrients salts in a sterile aqueous solution, thereby, providing a nutrient solution conducive to plant cell growth, injecting laboratory cultured starter or seed cells into the nutrient solution, saturating an inert, non-ionic liquid, preferably a polyorganosiloxane or flourocarbon with carbon dioxide gas, mixing the carbon dioxide saturated inert liquid with the aqueous cell suspension to provide via the absorbed carbon dioxide, carbon sufficient for predetermined cell growth quantity, adjusting and retaining the temperature of the multi-media mixture between 20° C. and 30° C., mixing the multi-media suspension at a rate not mechanically destructive of cells, providing photosynthesis light energy at an intensity of from 100 to 2,000 foot candles at the liquid surface, removing carbon dioxide spent inert liquid and replacing said liquid with renewed carbon dioxide saturated liquid periodically, as required to satisfy mitosis and separating and removing cells from the liquid.

* * * * *